United States Patent [19]

Merger et al.

[11] Patent Number: 4,594,461

[45] Date of Patent: Jun. 10, 1986

[54] PREPARATION OF TRIMETHYLOLALKANES FROM ALKANALS AND FORMALDEHYDE

[75] Inventors: Franz Merger, Frankenthal; Peter Hettinger, Edingen-Neckarhausen; Leopold Hupfer, Friedelsheim; Juergen Paetsch, Wachenheim, all of Fed. Rep. of Germany

[73] Assignee: BASF Aktiengesellschaft, Ludwigshafen, Fed. Rep. of Germany

[21] Appl. No.: 668,026

[22] Filed: Nov. 5, 1984

[30] Foreign Application Priority Data

Nov. 11, 1983 [DE] Fed. Rep. of Germany ....... 3340791

[51] Int. Cl.$^4$ ............... C07C 29/14; C07C 29/80; C07C 29/38; C07C 31/22
[52] U.S. Cl. ................................. 568/853; 568/854
[58] Field of Search .............................. 568/853, 854

[56] References Cited

U.S. PATENT DOCUMENTS

| | | | |
|---|---|---|---|
| 2,400,724 | 5/1946 | Walker | 568/854 |
| 3,201,480 | 8/1965 | Danzinger et al. | 568/853 |
| 3,808,280 | 4/1974 | Merger et al. | 568/853 |
| 4,247,485 | 1/1981 | Immel et al. | 568/464 |

FOREIGN PATENT DOCUMENTS

| | | |
|---|---|---|
| 1952738 | 7/1970 | Fed. Rep. of Germany . |
| 1535826 | 12/1978 | United Kingdom . |

*Primary Examiner*—J. E. Evans
*Attorney, Agent, or Firm*—John H. Shurtleff

[57] ABSTRACT

Trimethylolalkanes are prepared by reacting an n-alkanal with formaldehyde and a trialkylamine in aqueous solution and then hydrogenating the product, by a method in which from 2.2 to 4.5 moles of formaldehyde and from 0.6 to 3 moles of trialkylamine are used per mole of the alkanal, and the reaction mixture is worked up by distillation either before or after the hydrogenation.

11 Claims, No Drawings

PREPARATION OF TRIMETHYLOLALKANES FROM ALKANALS AND FORMALDEHYDE

The present invention relates to a process for the preparation of trimethylolalkanes by reacting an n-alkanal with formaldehyde and a trialkylamine.

It is known that trimethylolpropane can be prepared by reacting n-butyraldehyde with formaldehyde in an aqueous medium in the presence of an alkaline agent, such as sodium hydroxide. The dimethylolbutanal formed as an intermediate in this process, which is described in, for example, German Published Application DAS No. 1,154,080, undergoes a Cannizzaro reaction with formaldehyde and the alkali to give trimethylolpropane and a formate. The disadvantage of this process is that formates are formed as by-products in stoichiometric or greater amounts. Because of their decomposing effect, the salts have to be completely separated off before the trimethylolalkanes are purified by distillation; this gives rise to considerable environmental problems.

The preparation of pure trimethylolpropane cannot be carried out satisfactorily in this manner because substantial amounts of formaldehyde undergo a Cannizzaro reaction with the alkanal in the presence of the base, and mixtures of components which are difficult to separate are formed.

German Laid-Open Application DOS No. 1,952,738 describes a process for the preparation of trimethylolpropane in which n-butyraldehyde is reacted with aqueous formaldehyde in the presence of a tertiary organic amine. In this process, the amount of formaldehyde used is more than the five-fold molar amount, based on n-butyraldehyde. The tertiary amine is added in excess of the stoichiometric amount with the object of separating off the salt in a simpler manner. The excess formaldehyde is removed by means of a technically complicated distillation under superatmospheric pressure. The process is also unsatisfactory with regard to the yield and purity of the trimethylolpropane.

According to German Published Application DAS No. 2,507,461, trimethylolpropane can be prepared by reacting n-butyraldehyde with formaldehyde in the presence of a catalytic amount of a special branched tertiary alkylamine, such as dimethylaminoneopentanol, purifying the resulting dimethylolbutanal by distillation and then subjecting it to catalytic hydrogenation. This process gives unsatisfactory yields of trimethylolpropane. If, in this process, the basic catalyst is replaced by, for example, triethylamine, greatly reduced yields are obtained (cf. German Published Application DAS No. 2,507,461, Comparative Examples 2 and 3).

According to German Laid-Open Application DOS No. 2,813,201, better results can be obtained using a trialkylamine as the catalyst only in the presence of a large excess of formaldehyde. In this process it is necessary to use from 5 to 30 moles of formaldehyde and from 0.01 to 0.5 mole of the trialkylamine per mole of n-butyraldehyde. This process is not very suitable for an economical preparation of trimethylolpropane, since the large excess of formaldehyde has to be separated off before the catalytic hydrogenation. Moreover, the yields are unsatisfactory.

When trimethylolalkanes are produced using such a large excess of formaldehyde, it is necessary, for economic reasons, to recover the formaldehyde, which requires a technically very complicated procedure; it was therefore necessary to find a process which permits trimethylolalkanes to be prepared in good yield and high purity in an economically simpler manner.

In the novel process, which permits this advantageous preparation, the production of trimethylolalkanes by reacting an n-alkanal with formaldehyde and a trialkylamine in aqueous solution at as high as 120° C. and then hydrogenating the product is carried out by a method in which from 2.2 to 4.5 moles of formaldehyde and from 0.6 to 3 moles of trialkylamine are used per mole of the alkanal, and the reaction mixture is worked up by distillation either before or after the hydrogenation.

Examples of suitable n-alkanals are 3-ethyl-, 3-n-propyl-, 3-isopropyl-, 3-n-butyl-, 3-isobutyl-, 3-sec.-butyl- and 3-tert.-butylbutanal and the corresponding n-pentanals and n-hexanals of 8 carbon atoms, 4-ethyl-, 4-n-propyl- and 4-isopropylpentanals, 4-ethyl-n-hexanals, 5-ethyl-n-hexanals, 3-methylhexanal, 3-methylheptanal, 4-methylpentanal, 4-methylheptanal, 5-methylhexanal, 5-methylheptanal, 3,3,5-trimethyl-n-pentyl-, 3,3-dimethyl-n-butyl-, 3,3-dimethyl-n-pentyl-, 4,4-dimethylhexyl-, 4,5-dimethylhexyl-, 3,4-dimethylhexyl-, 3,5-dimethylhexyl-, 3,3-dimethylhexyl-, 3-methyl-4-ethylpentyl-, 3,3,4-trimethylpentyl- and 3,4,4-trimethylpentylaldehyde. Propanal, n-butanal, n-pentanal, 3-methylbutanal, n-hexanal, 3-methylpentanal, n-heptanal, 4-methylhexanal and n-octanal are preferred.

Examples of trialkylamines are trimethylamine, triethylamine, tri-n-propylamine and tri-n-butylamine. From 2.2 to 4.5, preferably from 2.5 to 4, in particular from 2.75 to 3.5, moles of formaldehyde and from 0.6 to 3, preferably from 0.7 to 2, in particular from 0.8 to 1.5, moles of trialkylamine are employed per mole of the alkanal.

The reaction is carried out in general at as high as 120° C., preferably from 20° to 100° C., in particular from 40° to 80° C., under reduced, atmospheric or superatmospheric pressure, preferably atmospheric pressure, either batchwise or continuously. If required, organic solvents which are inert under the reaction conditions are also used, preferably readily water-miscible solvents, advantageously cyclic ethers, e.g. tetrahydrofuran or dioxane, esters, e.g. methyl acetate, ethyl acetate or methyl propionate, alkanols, e.g. ethanol or methanol, glycol, ethylene glycol monoethyl ether or methyl glycol.

The reaction time is about 0.5–24, preferably 1–10, in particular 1–7, hours.

The formaldehyde is advantageously employed as an aqueous solution, for example as a 10–50% strength by weight aqueous solution. The water content of the aqueous reaction mixture is, for example, from 50 to 85, preferably from 60 to 80, in particular from 65 to 75, % by weight.

The reaction mixture is worked up by distillation either before or after the hydrogenation. In the former case, the distillative working up procedure is carried out by distilling from the reaction mixture, advantageously under reduced pressure, first water and then free trialkylamine and the trialkylammonium formate formed during the reaction. The residue is taken up in water, and the aqueous mixture is subjected to hydrogenation. However, it is also possible to hydrogenate the aqueous reaction mixture before it has been worked up by distillation or after only some of the stated more readily volatile components have been removed by distillation.

The hydrogenation is carried out in a conventional manner, advantageously in aqueous solution at from 80° to 150° C. and under from 20 to 200 bar. Conventional hydrogenation catalysts are used, for example those which contain nickel, copper or noble metals, such as platinum or palladium. The catalysts can be supported catalysts and may be used in suspension or by the fixed-bed procedure. Particularly suitable catalysts of the stated type are described in, for example, German Laid-Open Application DOS No. 3,027,890.

After the hydrogenation, the hydrogenated aqueous solution is worked up, for example directly or after extraction with a solvent, e.g. ketones, esters or alcohols which are sparingly soluble in water, the working up procedure comprising distillation or crystallization. The trimethylolalkanes are obtained in very good yield and purity.

EXAMPLE 1

216 g (3 moles) of n-butyraldehyde, 1,200 g of 30% strength formalin solution (12 moles of formaldehyde), 450 g (4.5 moles) of triethylamine and 1,000 g of water are combined and the mixture is kept at 70° C. for 4 hours, after which first the water and free triethylamine and then the triethylammonium formate (bp. 110° C./20 mbar) formed during the reaction are distilled off under reduced pressure (20 mbar). The residue is mixed with an equal weight of water, and the mixture is subjected to continuous hydrogenation at 120° C. and under 60 bar, the hydrogenation catalyst consisting of CuO and $Al_2O_3$ with an atomic ratio of Cu to Al of 0.75:1. After the mixture has been worked up by distillation, 342 g (85% yield) of trimethylolpropane of boiling point 153° C./3 mbar and 28 g (7.6% yield) of di-trimethylolpropane of boiling point 185° C./3 mbar are isolated, the % yields being based on n-butyraldehyde.

EXAMPLE 2

216 g (3 moles) of n-butyraldehyde are added dropwise to a mixture of 450 g (4.5 moles) of triethylamine, 1,200 g of 30% strength formalin solution (12 moles of formaldehyde) and 1,000 g of water in the course of 45 minutes, after which the solution is heated at 70° C. for 4 hours. Water, triethylamine and triethylammonium formate are distilled off under reduced pressure as described in Example 1, and the residue is then diluted with four times its weight of water and hydrogenated at 100° C. and under 100 bar, in the presence of 24 g of 10% strength Pd/carbon, in an autoclave. The absorption of hydrogen is complete after 3 hours. The catalyst is filtered off and the low boilers are separated off by distillation, after which 334 g (83% yield) of trimethylolpropane of boiling point 153° C./3 mbar and 26 g (7% yield) of di-trimethylolpropane of boiling point 185° C./3 mbar are isolated by distillation under 3 mbar, the stated % yields being based on n-butyraldehyde.

EXAMPLE 3

72 g (1 mole) of n-butyraldehyde are added dropwise to a mixture of 700 g of 15% strength formalin solution (3.5 moles of formaldehyde) and 150 g (1.5 moles) of triethylamine in the course of 20 minutes, after which the mixture is stirred for 5 hours at 73° C. The homogeneous solution is fed to a continuous hydrogenation at 120° C. and under 50 bar, the hydrogenation catalyst consisting of 81.47% of NiO and 18.53% of $Al_2O_3$, and the reacted mixture is distilled under reduced pressure. Low boilers and triethylammonium formate are separated off under 2.0 mbar, after which 110 g (82% yield) of trimethylolpropane and 18 g (14% yield) of di-trimethylolpropane are isolated by distillation under reduced pressure as described in Example 2, the stated % yields being based on n-butyraldehyde.

EXAMPLE 4

98.7 ml (0.71 mole)/hour of triethylamine, 42.9 ml (0.49 mole)/hour of n-butyraldehyde and 308.7 ml/hour of 15.2% strength formaldehyde solution (1.7 moles/hour of formaldehyde) are passed into a continuous reaction cascade which consists of three flasks connected in series, the reaction volume of each flask being 900 ml and the reaction temperature in each flask being 80° C. The reacted mixture from the cascade is fed to a continuous hydrogenation apparatus and is hydrogenated at 115° C. and under 60 bar, the catalyst consisting of 81.47% of NiO and 18.53% of $Al_2O_3$. Low boilers, and triethylammonium formate formed in the course of the reaction, are then separated off by distillation under reduced pressure (20 mbar). Fractional distillation of the residue under 3 mbar gives 125 g (84% yield) of trimethylolpropane per of hydrogenated mixture and 18 g (13% yield) of di-trimethylolpropane per of hydrogenated mixture, the stated % yields being based on n-butyraldehyde.

EXAMPLE 5

144 g (2 moles) of n-butyraldehyde are added dropwise to a stirred mixture of 550 g of 30% strength formalin solution (5.5 moles of formaldehyde), 302 g (3 moles) of triethylamine and 550 g of water in the course of 30 minutes, after which the mixture is heated at 72° C. for 4 hours. The reaction mixture is then hydrogenated continuously at 130° C. and under 50 bar, the catalyst consisting of 81.47% NiO and 18.53% of $Al_2O_3$. The low boilers and the resulting triethylammonium formate are then separated off by distillation under reduced pressure (20 mbar). Fractional distillation of the residue gives 203 g (76% yield) of trimethylolpropane of boiling point 153° C./3 mbar and 40 g (16% yield) of di-trimethylolpropane of boiling point 185° C./3 mbar, the stated % yields being based on n-butyraldehyde.

We claim:

1. A process for the preparation of a trimethylolalkane which comprises:
   reacting an n-alkanal with formaldehyde and a trialkylamine in aqueous solution at a temperature of from 40° C. up to about 120° C., using from 2.2 to 4.5 moles of formaldehyde and from 0.6 to 3 moles of trialkylamine per mole of the alkanal,
   hydrogenating the resulting reaction mixture, and
   recovering the trimethylolalkane by distillation.

2. A process as claimed in claim 1, wherein from 2.5 to 4 moles of formaldehyde and from 0.7 to 2 moles of trialkylamine are used per mole of the alkanal.

3. A process as claimed in claim 1, wherein from 2.75 to 3.5 moles of formaldehyde and from 0.8 to 1.5 moles of trialkylamine are used per mole of the alkanal.

4. A process as claimed in claim 1 wherein the reaction mixture is hydrogenated directly after the reaction.

5. A process as claimed in claim 1 wherein the reaction is carried out at from 40° C. to about 80° C.

6. A process as claimed in claim 1 wherein the trialkylamine is selected from the group consisting of trimethylamine, triethylamine, tri-n-propylamine and tri-n-butylamine.

7. A process as claimed in claim 1 wherein the n-alkanal is selected from the group consisting of propanal, n-butanal, n-pentanal, 3-methylbutanal, n-hexanal, 3-methylpentanal, n-heptanal, 4-methylhexanal and n-octanal.

8. A process as claimed in claim 1 wherein the n-alkanal is n-butanal.

9. A process as claimed in claim 6 using from 2.5 to 4 moles of formaldehyde and from 0.7 to 2 moles of trialkylamine per mole of the alkanal.

10. A process as claimed in claim 7 wherein the reaction is carried out at from 40° C. to about 80° C.

11. A process as claimed in claim 7 wherein the trialkylamine is selected from the group consisting of trimethylamine, triethylamine, tri-n-propylamine and tri-n-butylamine.

* * * * *